US012016672B2

(12) United States Patent
Alshaer (10) Patent No.: US 12,016,672 B2
(45) Date of Patent: Jun. 25, 2024

(54) METHOD AND SYSTEM FOR INDICATING OBSTRUCTIVE SLEEP APNEA DURING WAKEFULNESS

(71) Applicant: Hisham Alshaer, Mississauga (CA)

(72) Inventor: Hisham Alshaer, Mississauga (CA)

(*) Notice: Subject to any disclaimer, the term of this patent is extended or adjusted under 35 U.S.C. 154(b) by 538 days.

(21) Appl. No.: 16/935,220

(22) Filed: Jul. 22, 2020

(65) Prior Publication Data
US 2021/0022644 A1    Jan. 28, 2021

Related U.S. Application Data

(60) Provisional application No. 62/876,992, filed on Jul. 22, 2019.

(51) Int. Cl.
*A61B 5/08*    (2006.01)
*A61B 5/00*    (2006.01)
(Continued)

(52) U.S. Cl.
CPC .......... *A61B 5/0826* (2013.01); *A61B 5/087* (2013.01); *A61B 5/091* (2013.01); *A61B 5/7267* (2013.01);
(Continued)

(58) Field of Classification Search
CPC ....... A61B 5/0826; A61B 5/087; A61B 5/091; A61B 5/7267; A61B 5/7278;
(Continued)

(56) References Cited

U.S. PATENT DOCUMENTS

2008/0177195 A1* 7/2008 Armitstead .......... A61B 5/4818
600/529
2013/0289401 A1* 10/2013 Colbaugh ............ A61B 5/4818
600/536
(Continued)

OTHER PUBLICATIONS

Oracle Help Center. (Nov. 21, 2017). Retrieved Oct. 26, 2022, from https://docs.oracle.com/en/database/oracle/oracle-database/12.2/dmcon/support-vector-machines.html#GUID-DD64BD8A-201F-4487-A482-AA889BE04ACA (Year: 2017).*
(Continued)

*Primary Examiner* — Matthew Kremer
(74) *Attorney, Agent, or Firm* — Kevin J Fournier Intellectual Property Legal Services Ltd.; Kevin J Fournier (57) ABSTRACT

There is provided a computer-implemented device comprising a processor, a machine readable medium storing instructions, the instructions when executed by the processor for configuring the device for: receiving an airflow and volume signal from at least one airflow and volume sensor for a plurality of patients; digitizing the signal to a digital signal and segmenting the signal using a sliding window to extract a plurality of features from the digital signal comprising: peak-to-peak amplitude, root mean square, integral of the absolute values, zero-crossing rate, standard deviation of a first derivative, mean value; normalizing the plurality of extracted features; and, using the normalized plurality of extracted features and an input indicating sleep apnea severity to train a machine learning algorithm and generate a mathematical model for subsequent use in classifying airflow and volume sensed signals received for a particular patient during wakefulness as normal or sleep apnea.

6 Claims, 6 Drawing Sheets

(51) Int. Cl.
    *A61B 5/087* (2006.01)
    *A61B 5/091* (2006.01)
    *G16H 40/60* (2018.01)
    *G16H 50/20* (2018.01)

(52) U.S. Cl.
    CPC .......... *A61B 5/7278* (2013.01); *A61B 5/7282* (2013.01); *G16H 40/60* (2018.01); *G16H 50/20* (2018.01)

(58) Field of Classification Search
    CPC ... A61B 5/7282; A61B 5/4809; A61B 5/7264; A61B 5/4818; A61B 5/7239; A61B 5/7242; A61B 5/0816; A61B 2562/0204; A61B 5/4806; G16H 40/60; G16H 50/20; A61M 16/06
    See application file for complete search history.

(56) References Cited

U.S. PATENT DOCUMENTS

2019/0192047 A1* 6/2019 Stamatopoulos ....... G10L 25/66
2021/0401364 A1* 12/2021 Moussavi ............ A61B 5/7257

OTHER PUBLICATIONS

Ozdemir, Galip & Nasifoglu, Huseyin & Eroul, O. (2016). A Time-Series Approach to Predict Obstructive Sleep Apnea (OSA) Episodes. 10.11159/icbes16.117 (Year: 2016).*

Holmberg, E. B., Hillman, R. E., Perkell, J. S. (1988). Glottal airflow and transglottal air pressure measurements for male and female speakers in soft, normal, and loud voice. The Journal of the Acoustical Society of America, 84(2), 511-529. https://doi.org/10.1121/1.396829 (Year: 1988).*

G. C. Gutiérrez-Tobal, D. Álvarez, F. del Campo and R. Hornero, "Utility of AdaBoost to Detect Sleep Apnea-Hypopnea Syndrome From Single-Channel Airflow," in IEEE Transactions on Biomedical Engineering, vol. 63, No. 3, pp. 636-646, Mar. 2016, doi: 10.1109/TBME.2015.2467188. (Year: 2016).*

Berry, R. B., Koch, G. L., Trautz, S., Wagner, M. H. (2005). Comparison of respiratory event detection by a polyvinylidene fluoride film airflow sensor and a pneumotachograph in sleep apnea patients. Chest, 128(3), 1331-1338. https://doi.org/10.1378/chest.128.3.1331 (Year: 2005).*

* cited by examiner

Feature Normalization: Each feature vector is divided by the maximum value of that feature within the same subject.
Therefore, values will range between -1 and 1

METHOD AND SYSTEM FOR INDICATING OBSTRUCTIVE SLEEP APNEA DURING WAKEFULNESS

CROSS-REFERENCE TO RELATED APPLICATIONS

This application claims the priority of the U.S. provisional patent application No. 62/876,992 filed on 2019 Jul. 22.

FIELD OF THE INVENTION

The present invention relates to a method and system for indicating whether obstructive sleep apnea exists during wakefulness, and particularly using upper negative pressure measurements.

BACKGROUND OF THE INVENTION

Obstructive Sleep Apnea (OSA) is a common disorder, affecting almost 10% of adults, but very underdiagnosed. This is largely due to limited access to overnight sleep testing using polysomnography (PSG).

Obstructive Sleep Apnea (OSA) is a sleep breathing disorder characterized by recurrent cessations of breathing during sleep. Complete cessations are known as apneas whereas partial cessations are known as hypopneas. These events last 10-30 seconds on average and alternate with episodes of hyperventilation. Apneas and hypopneas are accompanied by intermittent reduction of blood oxygen levels (known as hypoxia) and arousals from sleep that cause sleep fragmentation and give rise to poor sleep quality. This in turn results in excessive daytime sleepiness, and impaired cognitive performance [1]. Interruption of breathing during sleep causes repetitive surges in blood pressure at night. This in turn increases the risk of developing daytime hypertension, and on the long run heart failure and stroke [2, 3]. Despite being a very common condition that affects at least 7-10% of adults and despite the associated morbidities and mortalities, it is largely underdiagnosed. It is estimated that almost 85% of patients with OSA remain undiagnosed [3, 4].

The current standard for diagnosing OSA is nocturnal polysomnography (PSG), in which patients sleep in a laboratory attached to electrodes that monitor sleep, breathing and arterial oxygen saturation ($SaO_2$). This is an expensive test with limited accessibility and long wait lists that must be performed by a trained technologists and is cumbersome for patients. Several attempts have been made to devise methods to diagnose OSA that are convenient and portable. Portable OSA monitors allow patients to be tested in the convenience of their homes. Yet, there is still a need for tools to provide immediate diagnosis of OSA, without the need for an overnight sleep test that can be used in outpatient clinics. Therefore, there is a dire need for new innovative methods to detect the presence and severity of OSA in awake patients without undergoing an overnight sleep test.

Additionally, many of the current testing for OSA relies on manual diagnosis and interpretation of results which can be inefficient and result in inaccuracies. There is therefore a need to provide an accurate automated method and system for efficiently diagnosing obstructive sleep apnea (OSA) during wakefulness.

SUMMARY OF THE INVENTION

In at least one embodiment, there is provided a computer-implemented method and system comprising a processor, a machine readable medium storing instructions, the instructions when executed by the processor for configuring the system for: receiving an airflow and volume signal from at least one airflow and volume sensor for a plurality of patients; digitizing the signal to a digital signal and segmenting the signal using a sliding window to extract a plurality of features from the digital signal comprising: peak-to-peak amplitude, root mean square, integral of the absolute values, zero-crossing rate, standard deviation of a first derivative, mean value; normalizing the plurality of extracted features; and, using the normalized plurality of extracted features and an input indicating sleep apnea severity to train a machine learning algorithm and generate a mathematical model for subsequent use in classifying airflow and volume sensed signals received for a particular patient during wakefulness as normal or sleep apnea.

In one embodiment, there is provided a computer program product for providing diagnosis of sleep apnea, the computer program product comprising a non-transitory computer-readable medium having computer-readable code embodied therein executable by a processor for performing a method for providing diagnosis of sleep apnea, the method comprising: receiving an airflow and volume signal from at least one airflow and volume sensor for a plurality of patients; digitizing the signal to a digital signal and segmenting the signal using a sliding window to extract a plurality of features from the digital signal comprising: peak-to-peak amplitude, root mean square, integral of the absolute values, zero-crossing rate, standard deviation of a first derivative, mean value; normalizing the plurality of extracted features; and, using the normalized plurality of extracted features and an input indicating sleep apnea severity to train a machine learning algorithm and generate a mathematical model for subsequent use in classifying airflow and volume sensed signals received for a particular patient during wakefulness as normal or sleep apnea.

Additional aspects and advantages of the present invention will be apparent in view of the description which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In order that the subject matter may be readily understood, embodiments are illustrated by way of examples in the accompanying drawings, in which:

FIG. 3A and FIG. 3B are exemplary airflow waveform graphs from 2 patients, prior, during, and after application of NP at −5 cm $H_2O$. FIG. 3A illustrates the waveform graph of healthy subjects with an AHI=0.6. FIG. 3B illustrates the waveform graph of a sleep apnea patient with an AHI=18.2. The dashed square denotes the period of NP application;

DETAILED DESCRIPTION

In one or more embodiments, there is disclosed a system and a method to distinguish Obstructive Sleep Apnea ("OSA") from healthy individual using a maneuver during wakefulness in combination with computer-implemented machine learning methods and systems.

The Upper Airway ("UA") of patient with OSA is known to be narrow and more collapsible than healthy individuals without OSA. The present invention uses this property as a basis of identifying OSA patients during wakefulness. Numerous studies have shown that the UA in OSA patients is more susceptible to collapse when exposed to suction of negative pressure (NP) via nose or mouth, in both wakefulness and sleep, than in subjects without OSA [5-7]. NP a safe and easy tool and can be performed in a short duration of <30 minutes. Therefore, the present disclosure examines airflow waveforms and find discrimination in the features extracted during application of NP during wakefulness in healthy and OSA patients. In at least some aspects, the application of NP to the UA is expected to induce a partial UA collapse resulting in distinct breathing patterns that can be associated with OSA.

The present invention is described in the following Examples, which are set forth to aid in the understanding of the invention, and should not be construed to limit in any way the scope of the invention as defined in the claims which follow thereafter.

Examples

In at least some examples, participants underwent an overnight Polysomnography (PSG) to determine their ground truth OSA severity. Separately, they were asked to breathe through a nasal mask or a mouth piece through which negative pressure (NP) was applied, during wakefulness. Airflow waveforms were acquired and several features were extracted and used to train various classifiers to predict OSA. The performance of each classifier and experimental setup was calculated. In at least some examples, preferred results were obtained using Random Forest classifier for distinguishing OSA from healthy individuals with a very good area under the curve of 0.80.

Accordingly, the present methods and systems utilize computer-implemented machine learning systems and methods and data obtained from negative pressure (NP) suction from patients to diagnose whether sleep apnea exists (e.g. OSA) during wakefulness.

Generally, negative pressure is suction created by a physical device such as fan, and/or Venturi apparatus, as described herein. It is transmitted to the upper airway (throat) using a hose connected to a face/nose mouth or a mouth piece. In one embodiment, it is measured by centimeters of water (cm $H_2O$). In one embodiment, the negative pressure can vary between −5 to −15 H2O.

The term Ground truth OSA used herein can refer to the presence or absence of OSA is determined during an overnight sleep test in a sleep laboratory, known as polysomnography (PSG), which is described herein. PSG is then scored offline to identify breathing cessations known as apnea and hypopnea. The total number of apneas and hypopneas is tallied and divided by sleep time in hours to get the apnea-hypopnea index (AHI) as described herein. In one embodiment, a person is said to have OSA if their AHI exceeds a certain threshold e.g. 5, 10, or 15. Therefore individuals are divided into OSA with and an AHI equal or greater than the threshold or normal if their AHI is below than the threshold. This classification derived from PSG serves as the standard.

A. Subjects

In one example, patients were recruited from the Centre for Sleep Health and Research at Toronto General Hospital, University Health Network. The protocol was approved by the local research ethics board and all subjects provided written informed consent. A total of 16 subjects were recruited and participated in the experiments.

B. Polysomnography

Subjects underwent overnight Polysomnography (PSG) using standard techniques and scoring criteria for sleep stages and arousals, including thoracoabdominal movements, airflow, electroencephalography, and arterial $O_2$ saturation. These waveforms were manually scored by a trained technician to detect respiratory events (apneas and hypopneas). OSA severity is quantified as the number of apneas and hypopneas per hour of sleep, known as the Apnea Hypopnea Index (AHI) as derived from PSG. AHI can range from 0 to 100 events/hr. A patient is said to have OSA, if his/her AHI is greater than 5 to 15, which varies according to jurisdiction and practice. In our application, we examined discrete AHI thresholds of 5, 10, 15, and 20 to define the presence of OSA.

C. Negative Pressure Experiments

On a separate day, subjects were tested in the Care Lab at Toronto Rehabilitation Institute, University Health Network, Toronto. Negative pressure was generated using an air amplifier, which is a hollow tube that operates by the Venturi effect. The air amplifier was connected to a nasal mask or a mouthpiece, which was attached to the patient as demonstrated in FIG. 1. The experiment consisted of two halves, one applying NP at −5 cm $H_2O$ and the other at −10 cm $H_2O$. In each half, there was a nasal mask trial and a mouthpiece trial.

Each trial consisted of an acclimation period of five resting breaths, followed by NP application at the beginning of an expiration. NP was held for 5-7 breathing cycles. Airflow was captured using one or more sensors, e.g. pneumotachograph connected to the mouthpiece or the nasal mask (see FIG. 1), which is then digitized at sampling rate of 50 Hz. Mouth/nose pressure was also recorded using the same parameters as a reference, as shown in FIG. 1.

D. Feature Extraction

Figure 1:
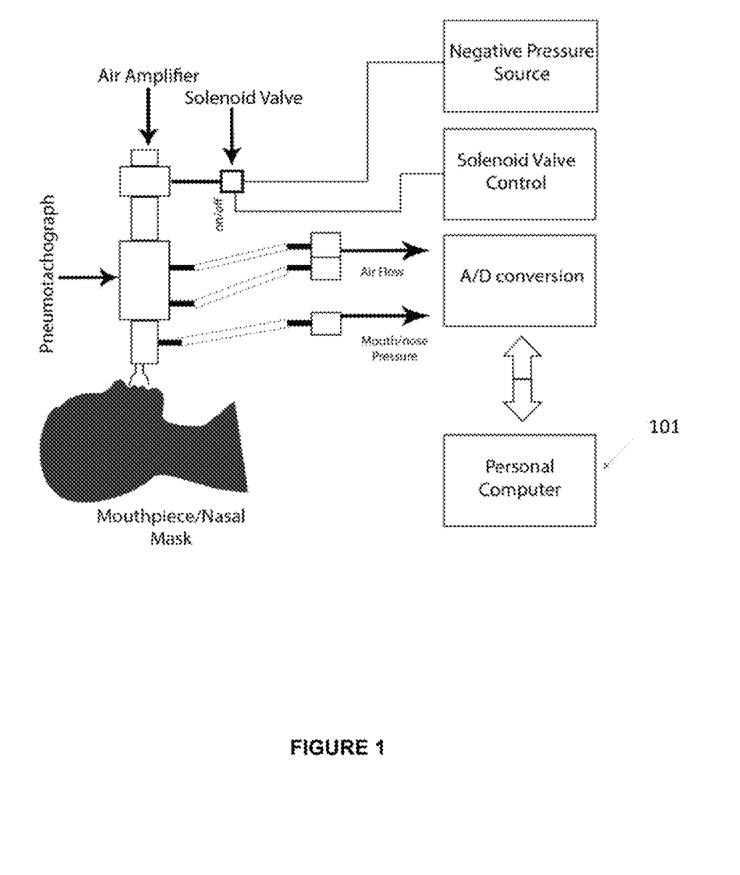
FIG. 1 is a schematic diagram illustrating the experimental setup used for inducing negative pressure and data collection from awake participants.
Figure 2:
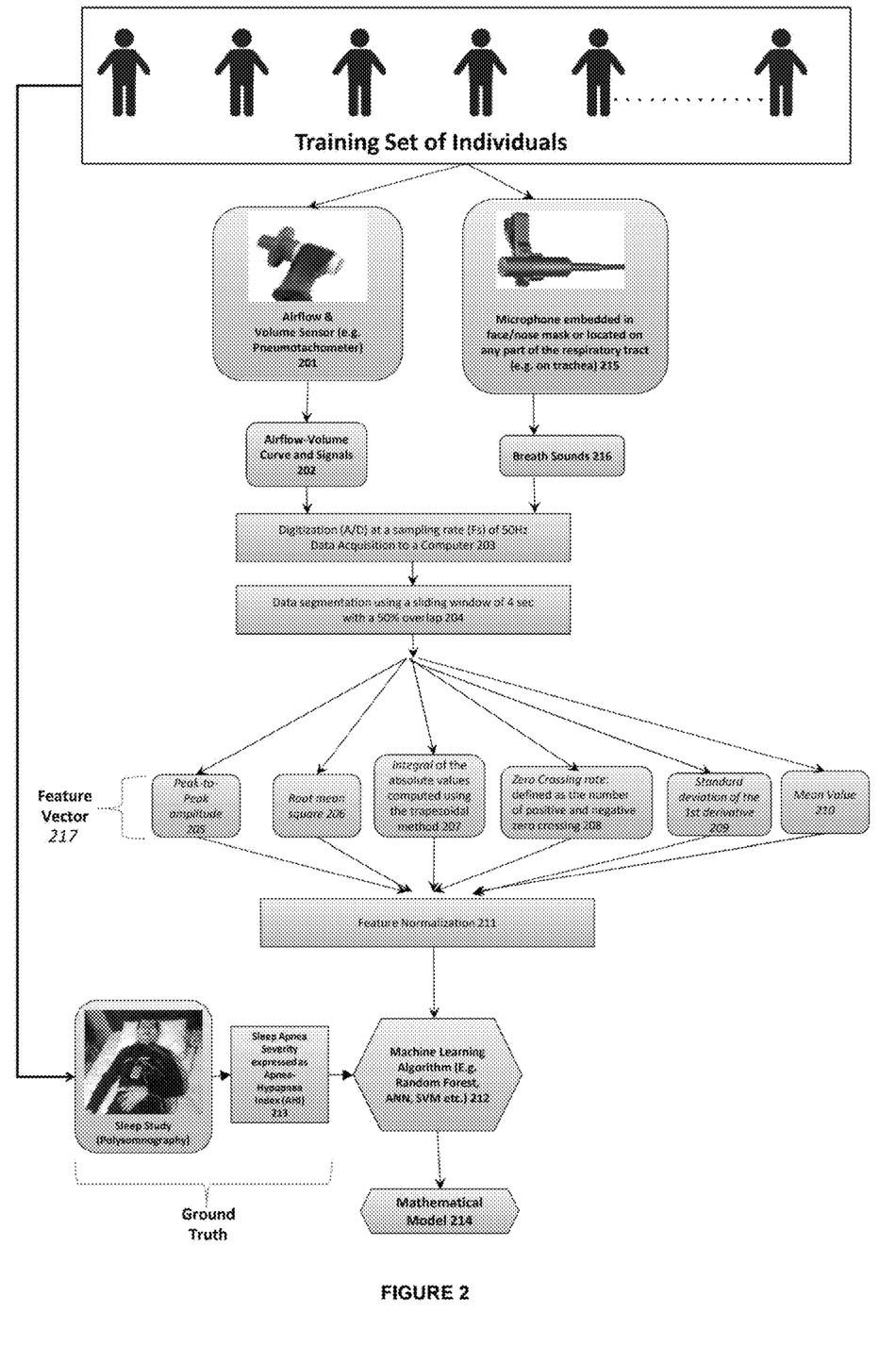
FIG. 2 is a flow diagram illustrating an example process of training a machine learning algorithm for generating a computer-implemented model to recognize sleep apnea.

Referring to FIGS. 1 and 2, in some embodiments, airflow signals (e.g. 202) acquired during the application of Negative Pressure (NP) (e.g. obtained from airflow and volume sensor 201) were used for feature extractions (e.g. steps 203 and 204 to generate feature vector set 205-210). In some examples, the feature extractions were performed directly without any signal conditioning. In at least one aspect, feature extraction is performed using a sliding window of 200 data points (4 seconds) with a 50% overlap (e.g. see step 204). Subsequently, the features of each subject were normalized (e.g. step 211) by their maximum value. The following features were computed from each window (data segmentation performed at step 204) to generate the feature vector set 217:

Peak-to-Peak amplitude (205): defined as the difference between the maximum and minimum values for each window.

Root mean square (206)

Integral of the absolute values (207) computed using the trapezoidal method

Zero Crossing rate (208): defined as the number of positive and negative zero crossing Standard deviation of the 1st derivative (209)

Mean value (210)

As may be envisaged by a person skilled in the art, additional features may be calculated and extracted from the airflow signal to provide additional feature in the feature vector set 217.

Figure 4:
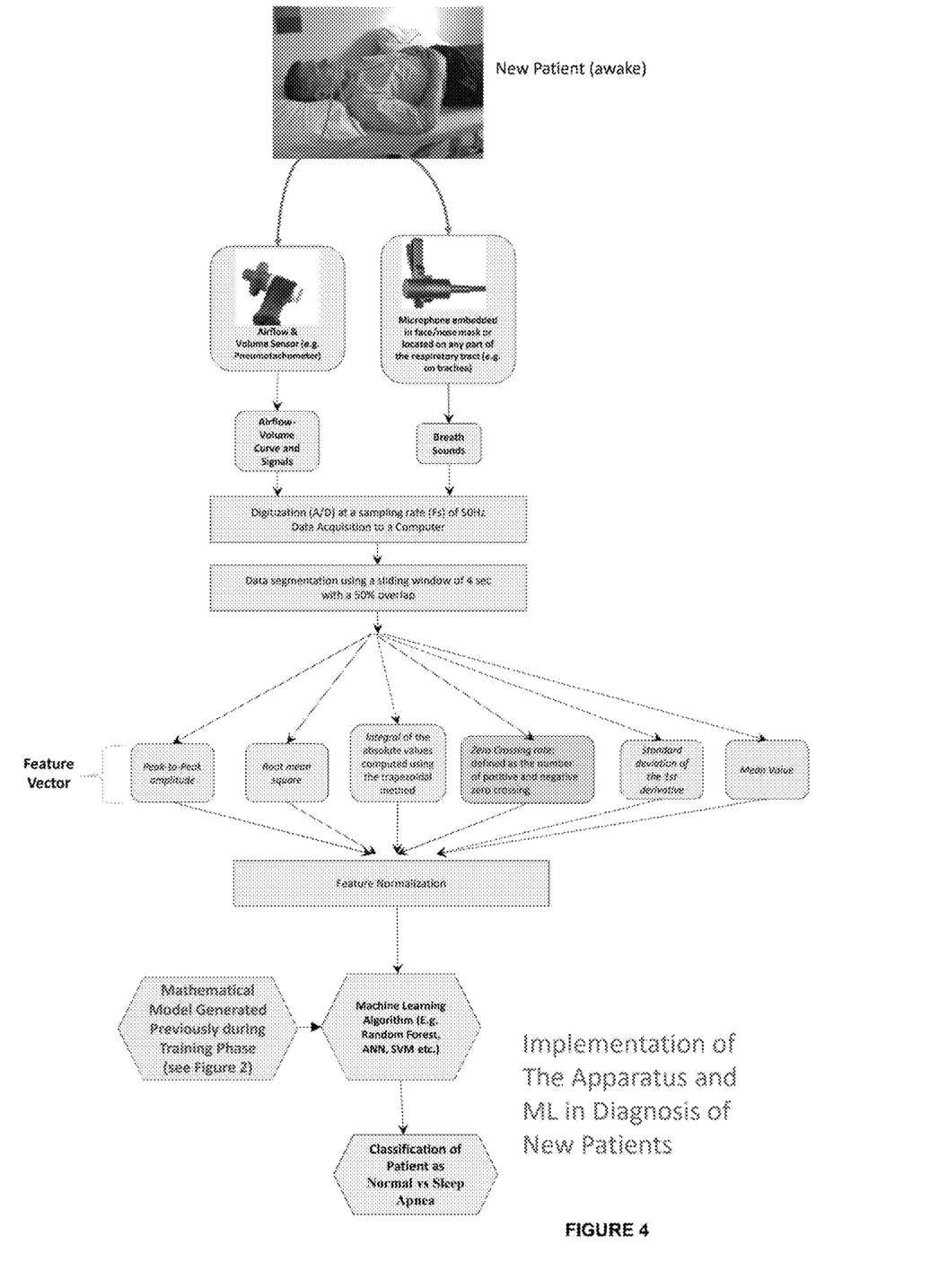
FIG. 4 is a flow diagram illustrating an example process of validating the computer-implemented model of FIG. 2 and applying it to machine learning algorithm to classify new patient(s) as having normal sleep diagnosis or sleep apnea diagnosis.
Figure 5:
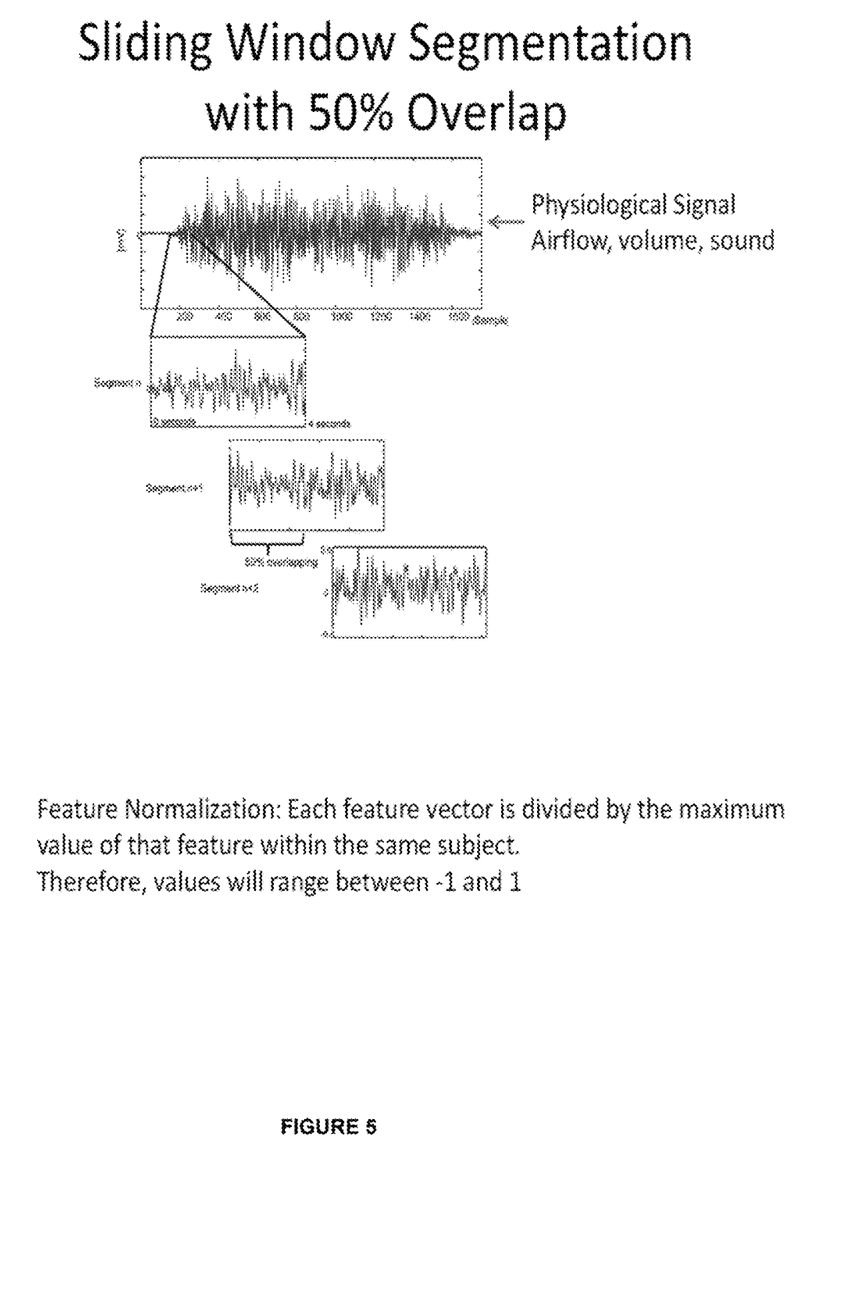
FIG. 5 illustrates example graphs of the output waveforms from the data segmentation block of FIG. 2 or FIG. 4; and, FIG. 6 is a schematic block diagram of the computing device (e.g. a personal computer) of FIG. 1 shown in further details.

Example graphs illustrating sliding window segmentation performed at step 204 of FIG. 2 (and also similarly performed in FIG. 4) are shown in FIG. 5. The graphs in FIG. 5 illustrate the physiological signal input (e.g. airflow, volume, sound.) being used by the data segmentation block at step 204 with a 50% overlap in order to extract desired vector feature set (e.g. set 217). As will be discussed, the retrieved feature set 217 is then normalized such that each feature vector set is divided by the maximum value of that feature within the same subject such that the values will range between −1 and 1.

In one aspect, illustrated in FIG. 2, additional data may be collected from patient(s) via one or more additional sensors for generating the extracted feature vector set 217. As illustrated in FIG. 2, the additional sensors may include a microphone embedded in the face/nose mask or located on any part of the respiratory tract as shown at step 215 for generating breath sounds 216 which are used in combination with the airflow-volume curve and signals at step 202 to be digitized at step 203 and segmented at step 204 for generating the feature vector set 217.

E. Machine Learning and Classification

Referring again to FIGS. 1 and 2, in one or more examples, the dataset of the recruited 16 subjects had a total of 1842 negative pressure data points (observations) collected from two locations (nose and mouth) using two pressure level (−5 and −10 cm $H_2O$). Referring to FIG. 2, in order to test the ability of the computer-implemented method and system (e.g. steps shown in FIG. 2) to distinguish OSA patients from healthy individuals (non-OSA), the Apnea-Hypopnea Index (AHI) thresholds of 5, 10, 15, 20 events/hr were used to define the presence of OSA. If a particular threshold is chosen, then every observation that has an AHI greater than that threshold is considered to be 'OSA class', and less than or equal to be 'healthy class'.

As shown in FIG. 2, the sleep apnea severity index AHI at step 213 along with the normalized extracted features at step 211 are provided to a machine learning algorithm 212 for training the algorithm with samples considered to be OSA class and healthy class and generate a mathematical model 214.

To validate the performance of the system, the following classifiers were deployed: Logistic Regression (LR), Support Vector Machine (SVM), and Random Forest (RF) (e.g. at step 212). The goal of this experiment was to find the optimal combination of location, pressure level and AHI that result in the best performance in detecting OSA across different subjects. For each classifiers, a leave-one-subject-out cross validation (LOSOCV) was performed. In this evaluation, data from (N−1) subjects was combined and classification models were trained on them, then the model was validated on the $N^{th}$ subject. This process is repeated N times and a combined performance metric was calculated. The advantage of this evaluation was that it is person independent and demonstrates the generalization capabilities of a classifier on an 'unseen subject' who is not included in training the classifier [8].

The Area Under the receiver operating curve (AUC) was used as the performance metric. After every fold of the cross-validation, the scores (or probabilities from a classifier) and the labels of the test set were concatenated with the previous fold. After the completion of N folds of LOSOCV, AUC is computed using these combined scores and labels, with OSA as the class of interest. An internal LOSOCV was also performed to find the best parameters for each of the classifiers. After finding the best parameters, each classifier (e.g. see step 212) was retrained on these parameters. The parameters and the range of values for each classifier were as follows:

LR: Lambda (regularization strength) $\hat{O}$ [0.01, 0.1, 1, 10, 100].

SVM: Kernel Scale $\hat{O}$ [0.01, 0.1, 1, 10, 100], Box Constraint $\hat{O}$ [0.01, 0.1, 1, 10, 100].

RF: Number of trees in ensemble $\hat{O}$ [10, 30, 50, 70, 90], Number of features to select at random for each decision split [f/4, f/2, 3f/4], where f=9 is the number of features.

Referring now to FIG. 4, shown are exemplary steps for evaluating whether a new patient, during wakefulness has sleep apnea or not. Steps are implemented similar to FIG. 2, other than the mathematical model generated in FIG. 2 (at step 214) is then applied onto the extracted feature set for the new patient using machine learning algorithm (e.g. neural network) to provide a classification output of the patient as being normal or sleep apnea.

Figure 6:
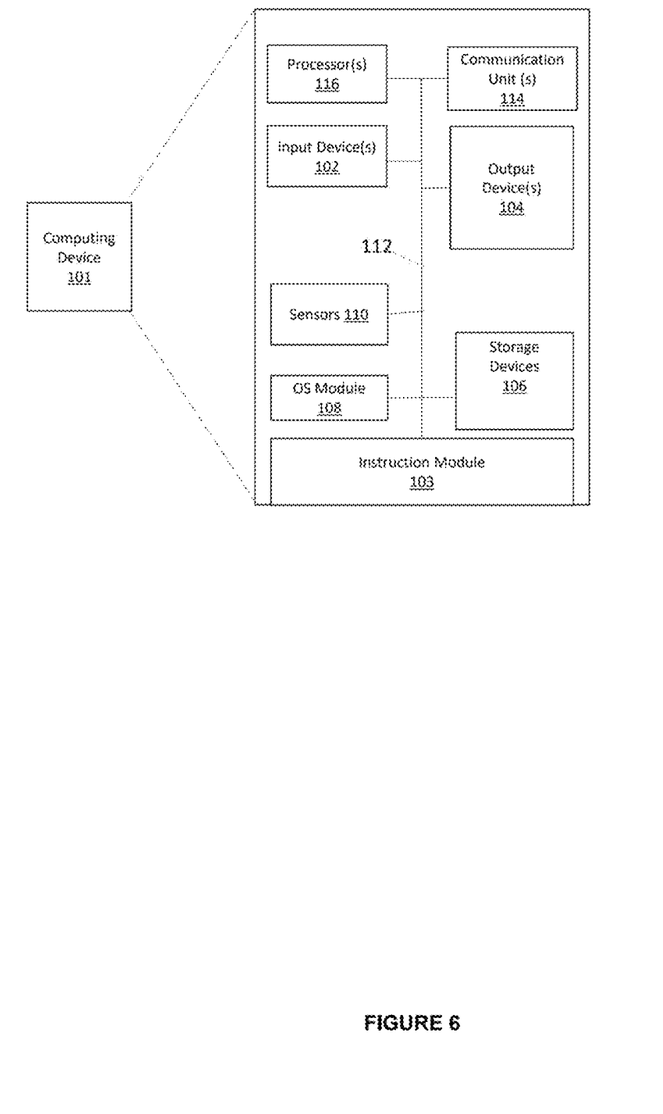

Referring to FIG. 6, shown is a simplified schematic block diagram illustrating the example computing components of the computing device 101 (e.g. personal computer of FIG. 1) for receiving physiological signals (e.g. airflow, volume, sound . . . ), extracting several relevant features (e.g. feature vector set 217) and using the extracted features for training a computer implemented machine learning model as per FIG. 2 for subsequent use (e.g. as per FIG. 4) in diagnosing obstructive sleep apnea (OSA) in an automatic and dynamic manner during wakefulness.

Computing device 101 comprises one or more processors 116, one or more input devices 102. Input devices 102 may be key pads, buttons, microphone or an optical input device, etc. Computing device 101 further comprises one or more output devices 104 which may include a display screen, a speaker, light, bell, vibratory device, etc. Device 101 also comprises one or more communication units 114 for communicating via one or more networks (not shown) to the computing components and/or sensors of FIG. 1. The device 101 further comprises one or more storage devices 106. The one or more storage devices 106 may store instructions and/or data for processing during operation of device 101, including instruction module 103 which includes one or more instruction component modules such as A/D converter, data segmentation, feature vector extraction, feature normalization, machine learning and classification. The one or more storage devices may take different forms and/or configurations, for example as short term memory or long term memory. Storage devices 106 may include internal memory to store instructions and/or data for device 101, which instructions when executed by the one or more processors 116 configure the device 101.

Computing device 101 also hosts an operating system (OS Module 108). The communication between the modules is performed by bus 112 and/or communication unit 114. Bus 112 may be a high-speed system interface or a high-speed peripheral interconnect bus, such as the PCI, PCI-express, or the like.

Referring to FIG. 6, the computing device 101 may comprise one or more of the sensors 110 of FIG. 1 (e.g. airflow and volume sensor) for monitoring various physiological data (e.g. airflow, breathing, . . . ) generating a signal based on monitoring the physiological data during wakefulness. The signal received and sensed by sensors 110 or via external sensors shown in FIG. 1 is converted by an A/D converter (e.g. as shown in FIG. 1) or an internal A/D converter provided by the instructions module 103. The instructions module 103, is configured to store instructions for, when executed by the one or more processors 116, extracting features from physiological signals (e.g. received from airflow and volume sensor, and/or microphone embedded in a face mask of the patient as shown in FIG. 2), digitizing the signals, performing data segmentation to extract features for training a machine learning algorithm and generating a machine learning model for subsequent classification of awake patients as having sleep apnea or normal. Accordingly, the instructions module 103 is configured to store instructions to perform the operations illustrated in FIGS. 2 and 4 relating to training and validation of the machine learning model developed (e.g. at step 214 of FIG. 2).

Computing device 101 can be a desktop personal computer, a laptop, a smartwatch, in other examples, it may be a mobile device such as a cell phone, a tablet, tabletop computer, etc.

Results

The disease distribution in the 16 recruited subjects were as following: 3 subjects had AHI <5; 4 subjects had AHI 5-10; 1 subject had AHI 10-15; 3 subjects had AHI 15-30; and 5 subjects had AHI ≥30.

Figure 3A:
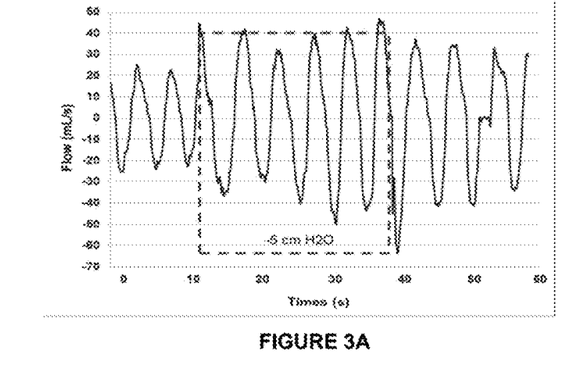
Figure 3B:
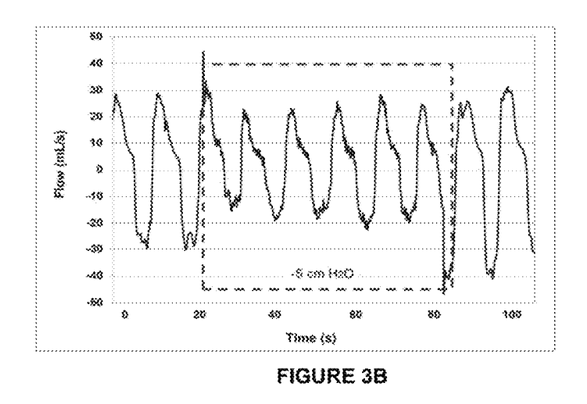

Airflow signals from participants along with the pressure data were acquired simultaneously. Upon NP application, airflow of individuals with low AHI tended to increase in peak-to-peak with smooth waveforms (see FIG. 3A). On the other hand, airflow acquired from individuals with higher AHIs was diminished during the application of NP. A high frequency ripple was generally observed in airflow of these patients during NP (see FIG. 3B).

Extracted features showed statistical difference in OSA from healthy individuals, when pooling features from all windows from all experiments. Among features listed in Section D (e.g. feature vector set 217), the 1$^{st}$ 3 features were highly significantly different between OSA and non-OSA individuals using a diagnostic AHI of 10 (p<0.0001). Similarly, when using a diagnostic AHI of 15, the 1$^{st}$ 4 features were statistically different (p<0.0001).

The results of employing three different classifiers on features collected at different locations, pressures and AHI thresholds were tabulated in Table 1. AUC is constructed by calculating sensitivity and specificity for detecting OSA at various AHI diagnostic thresholds, where a higher AUC denotes better performance. It can be observed that the best AUC was reported for RF classifier (0.801) for nose location, at pressure of −5 cm $H_2C$, with a diagnostic AHI of 10 events/hr.

TABLE 1

Table 1: illustrates the performance results of different classifiers for detecting Obstructive Sleep Apnea in wakefulness at different experiment locations, pressures, and AHI thresholds.

| Location | Pressure | AHI | AUC | | |
|---|---|---|---|---|---|
| | | | LR | SVM | RF |
| Mouth | 5 | 5 | 0.381 | 0.340 | 0.562 |
| | | 10 | 0.281 | 0.447 | 0.405 |
| | | 15 | 0.557 | 0.523 | 0.490 |
| | | 20 | 0.648 | 0.631 | 0.547 |
| | 10 | 5 | 0.154 | 0.498 | 0.410 |
| | | 10 | 0.434 | 0.255 | 0.454 |
| | | 15 | 0.399 | 0.473 | 0.450 |
| | | 20 | 0.278 | 0.394 | 0.453 |
| Nose | 5 | 5 | 0.370 | 0.494 | 0.622 |
| | | 10 | 0.364 | 0.575 | 0.801 |
| | | 15 | 0.345 | 0.615 | 0.449 |
| | | 20 | 0.274 | 0.618 | 0.357 |
| | 10 | 5 | 0.390 | 0.410 | 0.371 |
| | | 10 | 0.457 | 0.561 | 0.649 |
| | | 15 | 0.545 | 0.554 | 0.706 |
| | | 20 | 0.404 | 0.640 | 0.539 |

DISCUSSION

In at least some examples, the study results showed that the invention results in a very good distinction between patients with and without OSA based on features extracted from their airflow patterns upon the application of NP during wakefulness. A diagnostic AUC reaching 0.80 compared with the gold standard PSG was achieved. This illustrates at least one advantage of the current disclosed systems and methods, in at least some embodiments, using machine learning and Negative pressure data acquisition for airflow signals (e.g. as illustrated in FIG. 2).

In at least some embodiments, there are several factors that contributed to the good performance of the classification scheme. An important factor was the selection of the feature set. The features provided in feature vector set 217 were based on the underlying pathophysiology of obstructive sleep apnea. OSA patients are known to have relatively narrower upper airway (pharynx area). In addition, the muscles that control that segment of the airway don't have a normal tone, which predisposes them to collapse during sleep. The application of negative pressure during wakefulness challenges the upper airway tissues and muscles, thus exposes their ability to counteract this force. In normally functional airways, muscles counteract the suction effect by further dilating the airway to maintain normal flow. On the other hand, narrower airways with less functional muscles have lesser ability to maintain the patency of the airway, which results in tissue proximity and vibration. The latter is manifested by airflow instability and vibration as demonstrated in FIGS. 3A and 3B. The feature set (e.g. provided in step 217) is designed to harvest these phenomena. For example, the peak-to-peak values (e.g. 205) airflow quantify overall airflow amplitude, which is diminished in OSA patients. Similarly, the standard deviation of the 1$^{st}$ derivative quantified the high frequency ripple that results from tissue vibration in floppy and unstable tissues of OSA patients.

In at least some embodiments, the following three classifiers were used at step 212: LR, SVM, and RF. Preferably, random forest classifier is used at step 212 as it was proven more superior, in than the other classifier as shown by the noticeably higher AUC values obtained using RF. In at least some examples, RF classifier has proved the best for classification of breath sounds related sleep apnea during sleep. Although the experimental setup is different in this study and data were collected during wakefulness rather than sleep, the good performance of RF in both cases might be attributed to the similarity of physiological phenomenon and underlying mechanism between both studies. RF also allows more efficient computations and stronger discriminant power of the selected features. An AHI threshold of 10 gave the best performance, which is a diagnostic threshold widely used in the clinical practice. This threshold is probably the boundary between negligible and a more serious disease.

PSG has been the gold standard for diagnosing sleep apnea. However, it is an expensive procedure that requires the patient to spend a night in a sleep laboratory, which is uncomfortable and in many locales inaccessible. In order to overcome this limitation, several researchers have developed simple diagnostic tools for portable home monitoring of sleep apnea [10-13]. Yet, those methods still require and an overnight test.

The presently described systems and methods provide a tool which allows instantaneous diagnosis in outpatient settings, which can dramatically improve access to diagnosis and treatment.

In conclusion, the results obtained (e.g. see FIG. 4) show very good ability of the disclosed methods and systems using computer-implemented machine learning and classification to identify patients with OSA using data collected during wakefulness. These results for a new diagnostic modality that allows rapid diagnosis and treatment without the need for overnight sleep testing.

While the foregoing invention has been described in some detail for purposes of clarity and understanding, it will be appreciated by one skilled in the art, from a reading of the disclosure, that various changes in form and detail can be made without departing from the true scope of the invention in the appended claims.

All publications, patents, and patent applications are herein incorporated by reference in their entirety to the same extent as if each individual publication, patent or patent application was specifically and individually indicated to be incorporated by reference in its entirety.

It is contemplated that any part of any aspect or embodiment discussed in this specification can be implemented or combined with any part of any other aspect or embodiment discussed in this specification.

While particular embodiments have been described in the foregoing, it is to be understood that other embodiments are possible and are intended to be included herein. It will be clear to any person skilled in biomedical sciences and/or medicine and/or clinical decision support and/or machine learning algorithms that modifications of and adjustments to the foregoing embodiments, not shown, are possible.

REFERENCES

[1] H. C. Kim, T. Young, C. G. Matthews, S. M. Weber, A. R. Woodward, and M. Palta, "Sleep-disordered breathing and neuropsychological deficits. A population-based study," *Am J Respir Crit Care Med*, vol. 156, pp. 1813-9, December 1997.
[2] P. Kohli, J. S. Balachandran, and A. Malhotra, "Obstructive sleep apnea and the risk for cardiovascular disease," *Curr Atheroscler Rep*, vol. 13, pp. 138-46, April 2011.
[3] H. Alshaer, "A Single-Channel Acoustic Method For Portable Diagnosis of Sleep Apnea," PhD Thesis, Institute of Biomaterial and Biomedical Engineering, University of Toronto, Toronto, Canada, 2013.
[4] T. Young, J. Blustein, L. Finn, and M. Palta, "Sleep-disordered breathing and motor vehicle accidents in a population-based sample of employed adults," *Sleep, vol.* 20, pp. 608-13, August 1997.
[5] G. Insalaco, S. Romano, O. Marrone, A. Salvaggio, and G. Bonsignore, "A new method of negative expiratory pressure test analysis detecting upper airway limitation to reveal obstructive sleep apnea," *Chest*, vol. 128, pp. 2159-2165, 2005.
[6] G. Liistro, C. Veriter, M. Dury, G. Aubert, and D. Stanescu, "Expiratory flow limitation in awake sleep-disordered breathing subjects," *Eur Respir J*. pp. 185-190, 1999.
[7] E. Venin, C. Tardif, T. Similowski, P. Pasquis, and J. Muir, "Evidence for expiratory flow limitation of extrathoracic origin in patients with obstructive sleep apnea," *Thorax*, pp. 423-428, 2002.
[8] S. S. Khan, M. E, Karg, D. Kulie, and J. Hoey, "Detecting falls with x-factor hidden markov models," *Applied Soft Computing*, vol. 55, pp, 168-177, 2017.
[9] H. Alshaer, A. Pandya, T. Bradley, and R. Rudzicz, "Subject Independent Identification of Breath Sounds Components Using Multiple Classifiers," in 2014 *IEEE International Conference on Acoustics, Speech and Signal Processing (ICASSP)*, Florence, Italy, 2014, pp. 3577-3581.
[10] H. Alshaer, G. R. Fernie, E. Maki, and T. D. Bradley, "Validation of an automated algorithm for detecting apneas and hypopneas by acoustic analysis of breath sounds," *Sleep Med*, vol. 14, pp. 562-71, June 2013.
[11] H. Alshaer, G. R. Fernie, W. H. Tseng, and T. D. Bradley, "Comparison of in-laboratory and home diagnosis of sleep apnea using a cordless portable acoustic device," *Sleep Med*, vol. 22, pp. 91-6, June 2016.
[12] H. Alshaer. A. Levchenko, T. D. Bradley, S. Pong, W. H. Tseng, and G. R. Fernie, "A system for portable sleep apnea diagnosis using an embedded data capturing module," *J Clin Monit Comput*, vol. 27, pp. 303-11, June 2013.
[13] H. Alshaer, "New Technologies for the Diagnosis of Sleep Apnea," *Curr Hypertens Rev*, vol. 12, pp. 48-56, 2016.

What is claimed is:

1. A system for indicating whether obstructive sleep apnea exists during wakefulness, comprising:
    a plurality of sensors for detecting a plurality of signals including airflow signals, volume signals of the flow, and sound generated from a person during wakefulness;
    a communication unit;
    a computer; and
    a non-transitory computer readable medium comprising a program causing the computer to:
        i. receive the airflow and volume signals from the plurality of sensors;
        ii. digitize the airflow and volume signals to digital signals;
        iii. segment the digital signals using a bedded sliding window to extract a plurality of features from the digital signals;
        iv. normalize the plurality of extracted features;
        v. use the normalized plurality of extracted features and an input indicating sleep apnea severity to train a machine learning algorithm and generate a statistical model for subsequent use in classifying the airflow and volume signals received from the plurality of sensors for the person during wakefulness as normal or sleep apnea;

vi. receive second airflow and volume signals from the plurality of sensors;

vii. digitize the second signals received from the plurality of sensors to second digital signals;

viii. segment the second digital signals using the bedded sliding window to extract a second plurality of features from the second digital signals;

ix. normalize the second plurality of extracted features;

x. classify the second signals received from the plurality of sensors for the person during wakefulness as normal or sleep apnea using the statistical model generated by the trained machine learning algorithm; and xi. transmit via the communication unit an indication classifying the person as normal or prone to sleep apnea.

2. The system of claim 1, wherein steps i and vi additionally comprise receiving breath sounds and second breath sounds, respectively, while the subject is awake.

3. A method of indicating whether obstructive sleep apnea exists during wakefulness, the method being carried out on a system, the system comprising:

a plurality of sensors for detecting a plurality of signals including airflow signals, volume signals of the flow, and sound generated from a person during wakefulness;

a communication unit;

a computer; and a non-transitory computer readable medium comprising a program causing the computer to carry out the following steps of the method:

i. receive the airflow and volume signals from the plurality of sensors;

ii. digitize the airflow and volume signals to digital signals;

iii. segment the digital signals using a bedded sliding window to extract a plurality of features from the digital signals;

iv. normalize the plurality of extracted features;

v. use the normalized plurality of extracted features and an input indicating sleep apnea severity to train a machine learning algorithm and generate a statistical model for subsequent use in classifying the airflow and volume signals received from the plurality of sensors for the person during wakefulness as normal or sleep apnea;

vi. receive second airflow and volume signals from the plurality of sensors;

vii. digitize the second signals received from the plurality of sensors to second digital signals;

viii. segment the second digital signals using the bedded sliding window to extract a second plurality of features from the second digital signals;

ix. normalize the second plurality of extracted features;

x. classify the second signals received from the plurality of sensors for the person during wakefulness as normal or sleep apnea using the statistical model generated by the trained machine learning algorithm; and xi. transmit via the communication unit an indication classifying the person as normal or prone to sleep apnea.

4. The method of claim 3, wherein steps i and vi additionally comprise receiving breath sounds and second breath sounds, respectively, while the subject is awake.

5. A non-transitory computer readable medium comprising a program causing a computer to carry out steps of a method of indicating whether obstructive sleep apnea exists during wakefulness, the method being carried out on a system, the system comprising:

a plurality of sensors for detecting a plurality of signals including airflow signals, volume signals of the flow, and sound generated from a person during wakefulness;

a communication unit;

the computer; and the non-transitory computer readable medium;

wherein the steps of the method comprising:

i. receive the airflow and volume signals from the plurality of sensors;

ii. digitize the airflow and volume signals to digital signals;

iii. segment the digital signals using a bedded sliding window to extract a plurality of features from the digital signals;

iv. normalize the plurality of extracted features;

v. use the normalized plurality of extracted features and an input indicating sleep apnea severity to train a machine learning algorithm and generate a statistical model for subsequent use in classifying the airflow and volume signals received from the plurality of sensors for the person during wakefulness as normal or sleep apnea;

vi. receive second airflow and volume signals from the plurality of sensors;

vii. digitize the second signals received from the plurality of sensors to second digital signals;

viii. segment the second digital signals using the bedded sliding window to extract a second plurality of features from the second digital signals;

ix. normalize the second plurality of extracted features;

x. classify the second signals received from the plurality of sensors for the person during wakefulness as normal or sleep apnea using the statistical model generated by the trained machine learning algorithm; and xi. transmit via the communication unit an indication classifying the person as normal or prone to sleep apnea.

6. The non-transitory computer readable medium of claim 5, wherein steps i and vi additionally comprise receiving breath sounds and second breath sounds, respectively, while the subject is awake.

* * * * *